United States Patent
Fischer et al.

(10) Patent No.: US 8,979,878 B2
(45) Date of Patent: Mar. 17, 2015

(54) INSTRUMENT FOR THE SURGICAL REMOVAL OF A DEFECTIVE HEART VALVE

(75) Inventors: Harald Fischer, Weingarten (DE); Florian Hauck, Karlsruhe (DE)

(73) Assignee: ENDOSMART Gesellschaft fur Medizintechnik mbH (DE)

( * ) Notice: Subject to any disclaimer, the term of this patent is extended or adjusted under 35 U.S.C. 154(b) by 1544 days.

(21) Appl. No.: 12/021,396

(22) Filed: Jan. 29, 2008

(65) Prior Publication Data

US 2008/0188880 A1    Aug. 7, 2008

(30) Foreign Application Priority Data

Feb. 1, 2007 (DE) .......................... 10 2007 005 900

(51) Int. Cl.
| | |
|---|---|
| *A61B 17/32* | (2006.01) |
| *A61B 17/3207* | (2006.01) |
| *A61B 17/3205* | (2006.01) |
| *A61B 17/00* | (2006.01) |
| *A61F 2/24* | (2006.01) |

(52) U.S. Cl.
CPC . *A61B 17/320725* (2013.01); *A61B 17/320016* (2013.01); *A61B 17/32053* (2013.01); *A61B 2017/00243* (2013.01); *A61F 2/24* (2013.01)
USPC ......................................................... 606/170

(58) Field of Classification Search
USPC ................... 606/170, 167, 159; 623/2.11
See application file for complete search history.

(56) References Cited

U.S. PATENT DOCUMENTS

| | | | |
|---|---|---|---|
| 5,924,424 A | 7/1999 | Stevens et al. | |
| 6,764,494 B2 | 7/2004 | Menz et al. | |
| 6,830,584 B1 | 12/2004 | Seguin | |
| 7,201,761 B2 * | 4/2007 | Woolfson et al. | 606/170 |
| 7,815,676 B2 * | 10/2010 | Greenberg | 623/2.11 |
| 2003/0144689 A1 * | 7/2003 | Brady et al. | 606/200 |
| 2004/0034411 A1 * | 2/2004 | Quijano et al. | 623/2.11 |
| 2004/0116951 A1 | 6/2004 | Rosengart | |
| 2005/0075659 A1 * | 4/2005 | Realyvasquez et al. | 606/167 |
| 2005/0131438 A1 | 6/2005 | Cohn | |
| 2006/0224180 A1 * | 10/2006 | Anderson et al. | 606/200 |

FOREIGN PATENT DOCUMENTS

WO    2004/089250    10/2004

* cited by examiner

*Primary Examiner* — Kathleen Holwerda
*Assistant Examiner* — Sarah Simpson
(74) *Attorney, Agent, or Firm* — Salter & Michaelson

(57) ABSTRACT

An instrument for the surgical removal of a defective heart valve. The instrument has elements that can be collapsed, in which the instrument cutting elements are collapsed when the instrument is introduced into the surgical field and are covered by means of contact protective sheaths. The instrument cutting elements are formed as cutting ring halves that can fold in around a hinge axis, these cutting ring halves being elastically deformable during the folding-in process, whereby their deformation is achieved by fish joints that also serve to aid in mutually moving the contact protective sheaths onto each of two body members.

20 Claims, 2 Drawing Sheets

INSTRUMENT FOR THE SURGICAL REMOVAL OF A DEFECTIVE HEART VALVE

TECHNICAL FIELD

The invention relates to an instrument for the surgical removal of a defective heart valve.

BACKGROUND OF THE INVENTION

Such instruments are primarily used for a single task, i.e., only for the removal of the defective heart valve, but instruments of this type are also known that include additional functions, which make it possible, for example, to insert a new heart valve with the same instrument and in the same surgical procedure after the removal of the defective heart valve (see DE 600 17 189 T2, FIG. 1 therein, reference number 10 with the description belonging thereto).

It is also known to provide instruments of this type with catching devices and/or with filter screens that can be clamped on, for example, in order to prevent fragments of tissue that are freed during the surgical removal of a defective heart valve (which is also usually calcified) and/or material deposits from entering the bloodstream of the patient (see the above-named DE 600 17 189 T2, FIG. 1 therein, reference number 14 with the description belonging thereto).

All of these embodiments of the instruments always have as a basic function the removal of a defective heart valve, so that the invention described below can be basically applied to these instruments.

Also, the invention described below is independent of the respective surgical method by means of which the instrument is guided to the defective heart valve by its advancing (distal) end. This is true for both conventional surgical methods, which presume the opening of the thorax and the exposing of an access to the heart, as well as for surgical techniques that make possible a heart valve surgery with a far smaller stress for the patient with the use of catheters and endoscopes (so-called minimally invasive methods).

A method is also known as a minimally invasive surgical method, in which an instrument can be inserted according to the invention, in which a trocar, which is used as an instrument channel, is guided directly to the heart between the ribs of an unopened thorax and is moved through the muscle of the heart wall up to the defective heart valve, so that surgery can be performed via the trocar on the beating heart "pump" (i.e., without the connection of a heart-lung machine (see for this purpose U.S. Pat. No. 5,924,424).

The present invention proceeds from a prior art instrument, as is known from US 2005/0075659 A1 of instruments for the surgical removal of a defective heart valve (see therein FIGS. 2A to 2C with the description relating to it on page 2 starting with paragraph number [0037]).

The known instrument has two halves or body members arranged at an axial distance relative to one another at or on a guide rod or elongated member, and each body member is formed in the shape of a spirally wound cutting element around the axis of the instrument. The two body members can be moved axially relative to one another by means of the elongated member in such a way that their spiral cutting elements that are aligned opposite one another cut out a defective heart valve positioned between the two body members.

For the surgical introduction of the instrument into the surgical field, the spirally wound cutting elements can be collapsed radially, i.e., the cutting elements that are somewhat loosely wound in their initial form will be tightly wound, whereupon the radial distance between the outer winding and the instrument axis becomes small, and a contact protective sheath, which is narrow in diameter and fitted to the elongated member, can be moved onto the two body elements. This has the principal advantage that the advancing (distal) end of the instrument comprising the narrow, fitted contact protective sheath is moved through the defective heart valve by the width of the piece relatively without problem until it is in a position, in which one body member is found on one side of the defective heart valve and the other body member is found on the other side of the defective heart valve. Then the contact protective sheath is pulled off axially from the body members in this position of the instrument, so that their spirally wound cutting elements can be released. In this way, the radial distances between the spiral windings increase from the instrument axis until a diameter is achieved for the respective outer winding of the cutting element, which corresponds to the diameter of the defective heart valve to be cut out and to the diameter of the new heart valve that is subsequently to be surgically inserted.

The two body elements are then moved toward one another by means of the elongated member (to which one of the body elements is attached) and are guided by means of a tubular member for displacement on the elongated member (the other body element is attached to this tubular member) and the defective heart valve is cut out. Then the two body members can be rotated relative to one another in order to support the cutting process.

After cutting out the defective heart valve, the spiral cutting elements are brought back to their smaller radial diameter and the contact protective sheath is again moved onto the two body members, and this is done, in fact, prior to removing the instrument from the surgical field. Problems may occur when the contact protective sheath is again moved onto the two body members, since despite identical manual manipulations, spirally wound cutting elements may have different spiral configurations and thus different outer diameters. Reference is made to U.S. Pat. No. 5,924,424 (see page 3 therein under paragraph number [0041]) relative to this disadvantage of the known instruments.

Another disruption in the functionality of the above-named instruments results from the fact that the spirally wound cutting elements do not produce a geometrically circular cut, whereupon the subsequent surgical insertion of a new heart valve is made considerably difficult, especially since currently all mechanically produced heart valve prostheses have a circular base for attachment.

It is also a considerable disadvantage that the spirally wound cutting elements of the known instruments of this type do not cut out a defective heart valve as a one-part valve piece, but the valve piece is primarily "chipped off" between its spiral cutters. In this way, additional problems arise and it is necessary to arrange catching devices and/or filter screens in order to prevent the "chipped off" tissue fragments from entering the bloodstream of the patient.

OBJECT OF THE INVENTION

The object of the present invention consists of further developing the above-described instrument according to the preamble to the claim so that on the one hand, it maintains the surgical advantages that result from the fact that the cutting tools can be collapsed and expanded radially and that a contact protective sheath is used, so that on the other hand, however, it will be assured that the above-named disadvantages are avoided, i.e., that no problems occur during surgery when the contact protective sheath is moved onto the two body members again, so that disturbances in the functionality of the instrument do not occur due to undesired "chipping" of the defective heart valve, and that finally, the production of a true-to-size circular cut is also assured when the defective heart valve is removed, and thus the subsequent surgical insertion and attachment of a new heart valve is made possible without problem.

SUMMARY OF THE INVENTION

This object is achieved according to the invention in that the cutting elements of the body members are each formed of two semicircular halves of a cutting ring, and these halves are joined together at their ends to form a circular cutting ring via a single-axis hinge joint (=hinge axis), wherein each half of the cutting ring is made of an elastically deformable flat material strip (preferably of superelastic Nitinol) and each is pre-shaped true to size in edge-wise format to the semicircle diameter required in the radially expanded state, that the hinge axes of the cutting ring halves are aligned perpendicular to the axis of the elongated member and each is attached by means of the head end of an elastically deformable fish joint that is resistant to extension and compression, the fish joints extending in the longitudinal direction of the elongated member and each is mounted on the elongated member by its foot end, and that each cutting ring half is held by means of another elastically deformable fish joint that is resistant to extension and compression, extending in the longitudinal direction of the elongated member and mounted on the elongated member by its foot end, the head end of which is coupled to the center of the semicircle on the semicircular-shaped cutting ring halves in the expanded state, whereby this coupling and/or the elastically deformable fish joint of the cutting ring halves permit conducting a swivel movement of almost 90° around an axis running crosswise to the fish joint.

During use of the two body members (during use, the cutting ring of the respective body member is fully expanded in the radial direction and adjusted precisely to a circle), the inventive concept utilizes the dimensional stability of a flat material strip, which is pre-shaped by manufacturing techniques in edge-wise format to a semicircular arc. This pre-shaping is a deformation or strain reinforced in the material structure and therefore precisely dimensioned. The dimensional stability is supported by attaching the two ends of the respective semicircular arc to the above-named hinge axes, which in turn are each attached by the head end of a fish joint and are attached to the elongated member of the instrument in the axial direction. In addition, the respective center of the semicircular arc is also axially attached to the elongated member of the instrument by another fish joint, so that the axial position and the necessary precision of the cutting ring diameter of the two body members is also assured by means of these fish joints.

For the structural embodiments of the cutting rings of the body members, the instrument maker has professional knowledge of how to provide the cutting rings with a particular dimensional stability and a precise shape by special impressions in flat strip material (e.g., by longitudinal and crosswise creases). It is also within the scope of the knowledge of the person skilled in the art of instrument construction to make a selection of specific material properties and or to decide upon specific dimensions of the edge-wise format, i.e., of the edge cross section of the flat strip material to be processed.

The invention also teaches how the dimensionally stable cutting rings of the respective body members are to be collapsed during use to a smaller radial distance relative to the elongated member of the instrument. It is next essential for this that both the cutting ring halves as well as the fish joints are made of a flat strip material that possesses very good elastic properties despite the necessary dimensional stability (such as, e.g., superelastic Nitinol). The cutting ring halves are collapsed by a combined play on the fish joints.

A preferred embodiment of the invention provides that the fish joints, the head ends of which are coupled to the center of the cutting ring halves, are mounted in a stationary manner by their respective foot ends to the elongated member, and that the fish joints, the head ends of which attach the hinge axes, are mounted so that they can be axially moved and stopped by their respective foot ends at or on the elongated member.

The above-named bearing designs of the respective foot ends of the fish joints define a functional course when the cutting ring halves are collapsed, which is characterized in that the fish joints which attach the respective center of the semicircular arcs of the cutting ring halves remain in their axial position, while on the other hand, the fish joints whose head ends are joined with the hinge axes of the cutting ring can be moved and stopped axially, so that they bring about a folding in of the cutting ring around its hinge axes and simultaneously cause the cutting ring halves to deform to a half-shape of a constricted oval or similar shape around their centers held in the respective axial position.

Nevertheless, it must be mentioned here that the respective bearing designs on the foot side of the fish joints may also be configured in another way without thereby departing from the scope of the teaching of the present invention. For example, the foot ends of the fish joints that hold in position the respective center of the cutting ring halves may also be mounted so that they can be moved and stopped by means of a sliding block on the elongated member of the instrument. Also, if the foot ends of the fish joints that attach the hinge axes of the cutting rings are mounted so that they can be moved and stopped on the elongated member by means of a sliding block, then functional courses result during the process of collapsing the cutting ring halves, in which the necessary axial movement paths are distributed onto all fish joints and thus are shortened for each fish joint.

An embodiment for the bearing designs of the respective foot ends of the fish joints would also be possible in which the embodiment is realized by its kinematic reversal, i.e., the foot ends of the fish joints assigned to the hinge axes would be mounted in a stationary manner on the elongated member and the fish joints coupled to the center of the cutting ring halves would be mounted so that they could be axially moved and stopped. The cutting ring halves are then folded in by keeping the hinge axes of the cutting rings in their axial position and moving the centers of the cutting ring halves away from the hinge axes.

It is true for all of these possible embodiments for the bearing of the ends of the fish joints on the foot end that the axial movements made possible as a rule by sliding blocks at or on the elongated member are achieved by means of a push and press connecting rod or by means of a coaxial inner or outer sheath of the elongated member, which extends up to the handle of the instrument and can be actuated there manually. The latter is a manipulation that is common for surgical instruments.

Both in the expanded state of the cutting ring as well as in the collapsed state of the cutting ring halves, the fish joints configure meridians of a funnel-shaped body, which can be ideally utilized to push a contact protection sheath that fits closely to the elongated member relative to its diameter onto the cutting elements of the folded-in cutting ring halves. The smooth transitions of this funnel shape and the elastic yielding of the fish joints in the radial direction assure that a contact protection sheath can be moved onto and/or again pulled off the folded-in instrument cutting elements at any time (and even repeatedly during surgery).

A particularly advantageous embodiment of the invention provides that each body member of the instrument has its own contact protection sheath, which is mounted on the fish joints that are assigned to the respective body member and which can be moved onto these fish joints axially and counter to the contact protection sheath of the other body member.

Additional improvements of the instrument according to the invention are possible in that the diameter of the cutting ring of one body member is slightly larger than the diameter of the cutting ring of the other body member, such that the two cutting rings engage in one another with the formation of a narrow shearing gap when cutting out the defective heart valve positioned between them.

It can additionally be provided that the body members with their cutting rings can rotate relative to one another in such a way that the defective heart valve will be cut out by a rotating-punching process.

DESCRIPTION OF THE DRAWINGS

An example of embodiment of the invention will be described in more detail below on the basis of the drawings.

DETAILED DESCRIPTION

Figure 1:
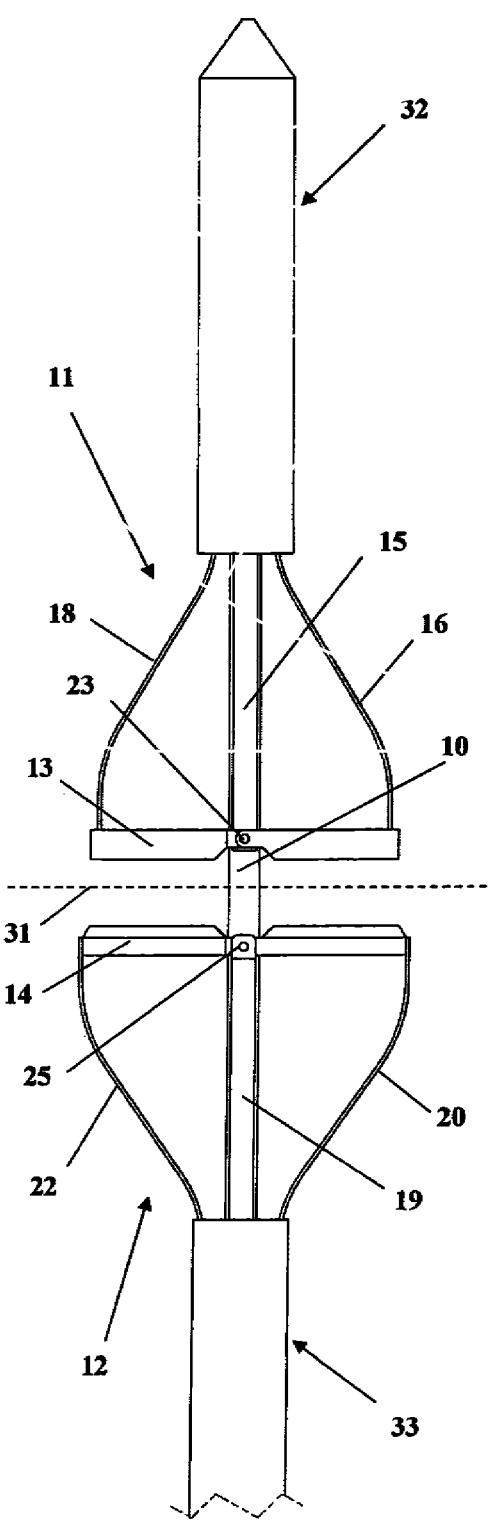
FIGS. 1 and 2 show in simplified representation the structure of the functional parts of an instrument according to the invention.
Figure 2:
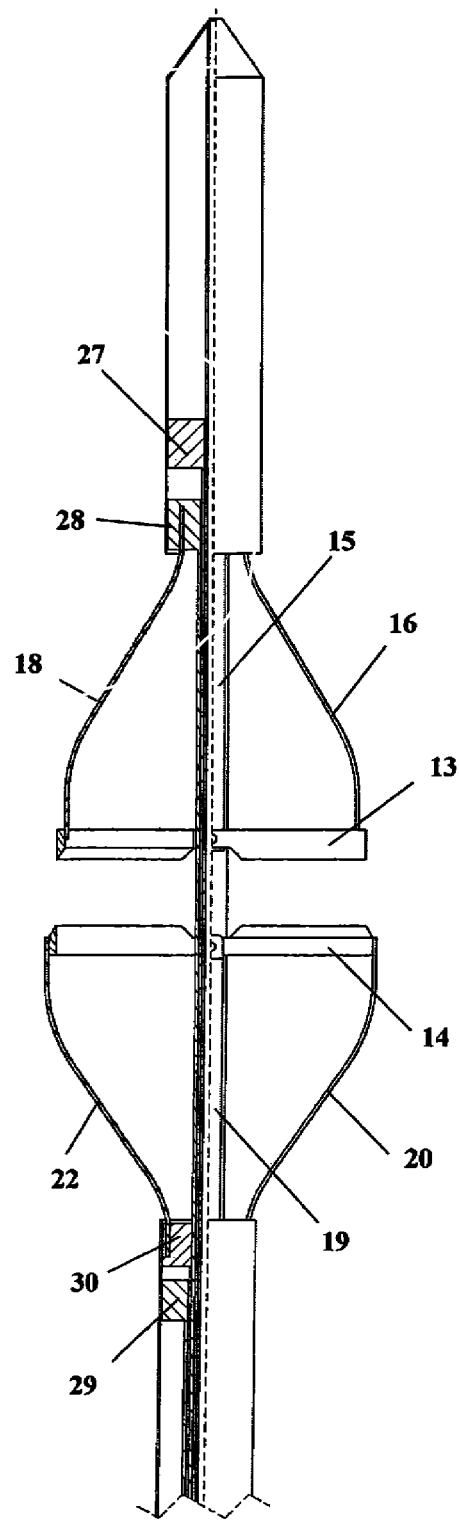
Figure 3:
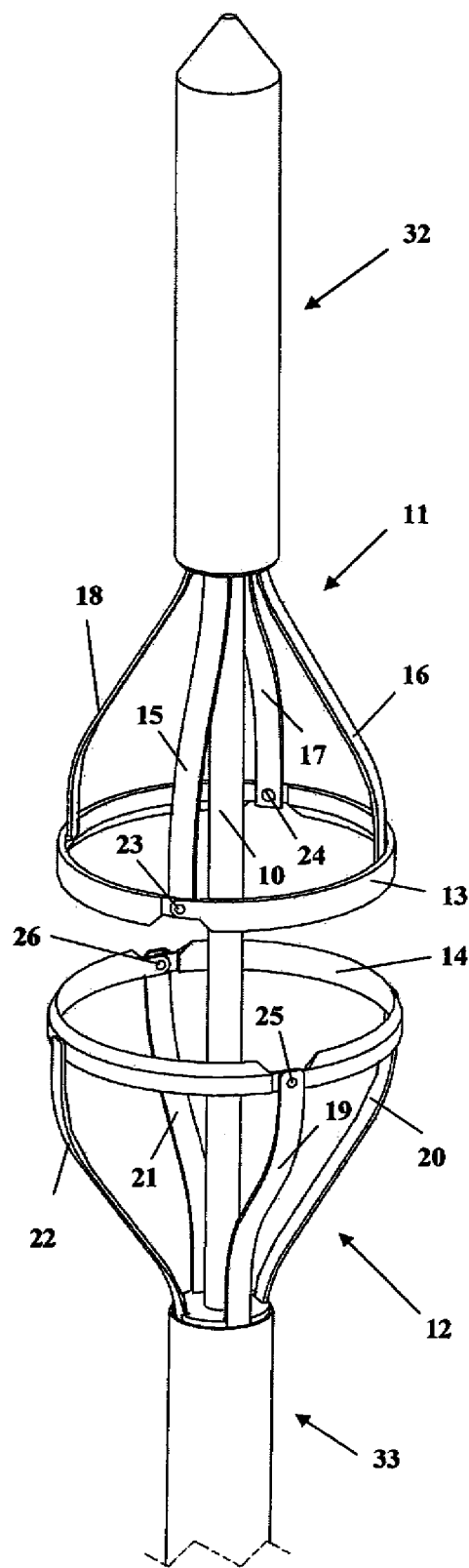
FIGS. 3 to 5 show in perspective representation the process of collapsing the cutting ring halves in an instrument according to FIGS. 1 and 2.

The basic construction of an instrument according to the invention is best seen from FIG. 3 in combination with FIGS. 1 and 2.

The central elongated member 10 can be recognized, which continues downward in the representations to an instrument handle, which is not shown in the figures, since it can be of usual structure and configuration. In and on such handle, various actuators and stopping mechanisms are present, by means of which the functional parts of the instrument, such as will be named below, can be individually controlled (adjusted) and/or stopped. This is usually performed by means of control rods running parallel to the elongated member and/or coaxial control sleeves guided into one another.

Two body members 11 and 12 that are formed in mirror image to one another are present coaxially around elongated member 10, each body member having a cutting ring 13 or 14, each with their four fish joints 15 to 18 or 19 to 22 for each ring, the fish joints each being mounted to elongated member 10 by their foot ends. The cutting rings are made of an elastically deformable flat strip material and are pre-shaped to a geometrically precise circular form. The fish joints are resistant to extension and compression in the longitudinal direction of the elongated member, but are elastically deformable in the radial direction to the elongated member with the introduction of corresponding radial force components.

The fish joints lying opposite one another in each body member, 15 and 17 (see upper body member) or 19 and 21 (see lower body member), attach their heads to hinge axes 23 and 24 or 25 and 26, respectively. The foot ends of fish joints 15 and 17 in the upper body member are attached in a sliding block 27 and the foot ends of fish joints 16 and 18 are attached to a bearing block 28 (see FIG. 2). The same applies to the lower body member, correspondingly for sliding block 29 and bearing block 30 (see FIG. 2).

The respective bearing blocks 28 and 30 are held in a stationary manner in their axial position, while on the other hand, sliding blocks 27 and 29 are mounted so that they can be moved and stopped axially on elongated member 10.

The upper body member 11 is moved toward the lower body member 12 by a rotation of elongated member 10, so that a defective heart valve, which is positioned in plane 31 between the two body members is cut out by means of a rotating-punching process (see FIG. 1), and by cutting rings 13 and 14 engaging in one another with the formation of a narrow shearing gap. The functional components used for rotating upper body member 10 are not shown in the figures for reasons of better clarity. They are of the usual structural type.

For folding in cutting rings 13 and 14 or their respective semicircular cutting ring halves, which are joined together by means of hinge axes 23+24 or 25+26, the fish joints 15+17 or 19+21 that are assigned to the respective hinge axes are moved in the axial longitudinal direction of the elongated member by means of their sliding blocks 27 or 29 on the foot side, and in the representation, this is at the top for the upper body member and at the bottom for the lower body member. These fish joints then assume the positions as shown in FIG. 4.

Figure 4:
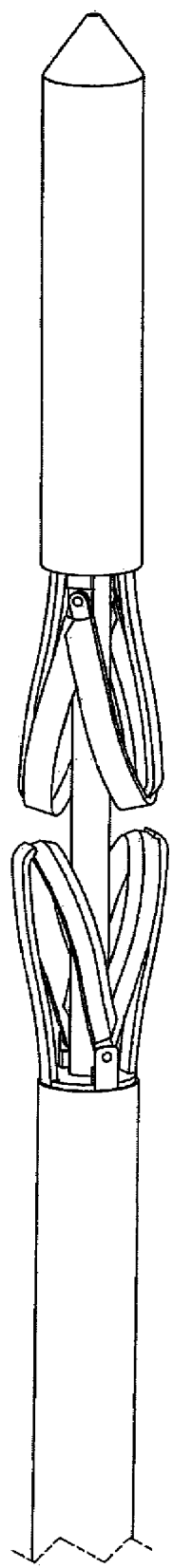

The other fish joints 18+16 of the upper body member and 20+22 of the lower body member maintain their respective axial positions, so that the respective cutting ring halves deform in the half-shape of an oval (or similar shape), as shown in FIG. 4.

Figure 5:
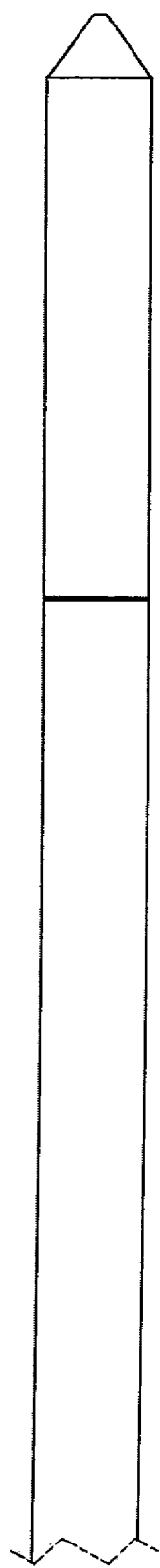

As a result, a collapsed state of the fish joints and of the cutting ring halves is then achieved, in which the two contact protective sheaths 32 and 33 each can be moved in the opposite direction and without problem onto the expanded or collapsed body members. FIG. 5 shows the state of the instrument according to the invention when it is completely closed by means of the contact protective sheaths.

The following documents that have been previously mentioned herein are all now incorporated by reference herein in their entirety: DE 600 17 189 T2; U.S. Pat. No. 5,924,424; US 2005/0075659

What is claimed is:

1. An instrument for the surgical removal of a defective heart valve, comprising:
   two body members arranged coaxially and at a distance to one another at or on an elongated member, these body members being able to move axially relative to one another by means of the elongated member, cutting elements aligned opposite one another to cut out a defective heart valve positioned between the body members,
   the cutting elements of the body members having a radially collapsed position, in which their radial distance from the instrument axis becomes smaller, for the surgical introduction of the instrument into the surgical field, and there is a contact protective sheath fitted to the elongated member, which is narrow in diameter, and which can be moved axially onto the body members having the radially collapsed cutting elements, so that an advancing end of the instrument comprises the contact protective sheath fitted to the elongated member, the sheath being narrow in diameter, is moved through the defective heart valve until it is in a position in which one body member is found on one side of the defective heart valve and the other body member is found on the other side of the defective heart valve, the contact protective sheath is pulled off axially from the body members in this position and the cutting elements of the body members have a radially expanded position, so that their radial distance from the instrument axis is increased up to a diameter that corresponds to the diameter of the defective heart valve to be cut out and to the diameter of a new heart valve that is subsequently to be inserted surgically, wherein the cutting elements of each of the body members are formed of two semicircular cutting ring halves each having a center, the cutting ring halves being joined to one another on the end to form a circular cutting ring by means of a single-axis hinge joint that is comprised of diametrically disposed hinge members having aligned respective hinge axes that together define a common swivel axis, wherein each half of the cutting ring is made of an elastically deformable flat material strip and each is pre-shaped true to size in edge-wise format to the diameter required in the radially expanded state, wherein the hinge axes of the respective hinge members of the cutting ring halves are aligned perpendicular to the axis of the elongated member and each respective hinge member is attached by means of a head end of an elastically deformable first fish joint that is resistant to extension and compression, the first fish joints each constructed of a flat material strip, extending in the longitudinal direction of the elongated member and each is mounted at the elongated member by a foot end thereof, and wherein each cutting ring half is held by means of another elastically deformable second fish joint that is resistant to extension and compression, each constructed of a flat material strip, extending in the longitudinal direction of the elongated member and mounted on the elongated member by the foot end thereof, the head end of which is connected to the center of the semicircular-shaped cutting ring halves in the extended state, whereby this coupling and/or the elastically deformable fish joints of the cutting ring halves permits conducting a relative swivel movement of the cutting ring halves of almost 90° around the common swivel axis folding between the radially collapsed position and the radially expanded position.

2. The instrument according to claim 1, wherein the second fish joints, the head ends of which are coupled to the center of the cutting ring halves, are mounted in a stationary manner by their respective foot ends to the elongated member, and the first fish joints, the head ends of which attach the hinge axes, are mounted so that they can be axially moved and stopped by their respective foot ends at or on the elongated member.

3. The instrument according to claim 1, wherein each body member possesses its own contact protective sheath, which is mounted onto the fish joints which are assigned to the respective body members, and which can be moved axially onto these fish joints and opposite to the contact protective sheath of the other body member.

4. The instrument according to claim 1, wherein a diameter of the cutting ring of one body member is slightly larger than a diameter of the cutting ring of the other body member, such that both cutting rings engage in one another with the formation of a narrow shearing gap when cutting out the defective heart valve positioned between them.

5. The instrument according to claim 1, wherein the body members with their cutting rings can rotate relative to one another in such a way that the defective heart valve will be cut out by a rotating-punching process.

6. The instrument according to claim 1, wherein the elastically deformable flat material strip is of superelastic Nitinol.

7. An instrument for the surgical removal of a defective heart valve comprising, an elongated member, two body members each having cutting elements and arranged coaxially and at a distance to one another at or on the elongated member, these body members being able to move axially relative to one another by means of the elongated member in such a way that the cutting elements aligned opposite one another cut out a defective heart valve positioned between the body members, the cutting elements of the body members having a radially collapsed position, in which their radial distance from the instrument axis becomes smaller, for the surgical introduction of the instrument into the surgical field, the cutting elements of each of the body members being formed of two semicircular cutting ring halves, each having a center and which are joined to one another on the end to form a circular cutting ring by means of a single-axis hinge joint that is comprised of diametrically disposed hinge members having aligned respective hinge axes that together define a common swivel axis, wherein each half of the cutting ring is made of an elastically deformable flat material strip and each is pre-shaped true to size in edge-wise format to a semicircle diameter required in the radially expanded state, wherein the hinge axes of the respective hinge members of the cutting ring halves are aligned perpendicular to the axis of the elongated member and each respective hinge member is attached by means of a head end of an elastically deformable first fish joint that is resistant to extension and compression, the first fish joints each constructed of a flat material strip, extending in the longitudinal direction of the elongated member and each is mounted at the elongated member by the foot end thereof, and wherein each cutting ring half is held by means of another elastically deformable second-fish joint that is resistant to extension and compression, the second fish joints each constructed of a flat material strip, extending in the longitudinal direction of the elongated member and mounted on the elongated member by a foot end thereof, the head end of which is connected to the center of the semicircular-shaped cutting ring halves in the extended state, whereby this coupling and/or the elastically deformable fish joint of the cutting ring halves permits conducting a relative swivel movement of the cutting ring halves around the common swivel axis folding between the radially collapsed position and the radially expanded position.

8. The instrument according to claim 7, wherein the second fish joints, the head ends of which are coupled to the center of the cutting ring halves, are mounted in a stationary manner by their respective foot ends to the elongated member, and wherein the first fish joints, the head ends of which attach the hinge axes, are mounted so that they can be axially moved and stopped by their respective foot ends at or on the elongated member.

9. The instrument according to claim 7, wherein each body member possesses its own contact protective sheath, which is mounted onto the fish joints which are assigned to the respective body members, and which can be moved axially onto these fish joints and opposite to the contact protective sheath of the other body member.

10. The instrument according to claim 7, wherein a diameter of the cutting ring of one body member is slightly larger than a diameter of the cutting ring of the other body member, such that both cutting rings engage in one another with the formation of a narrow shearing gap when cutting out the defective heart valve positioned between them.

11. The instrument according to claim 7, wherein the body members with their cutting rings can rotate relative to one another in such a way that the defective heart valve will be cut out by a rotating-punching process.

12. The instrument according to claim 7 wherein the elastically deformable flat material strip is of superelastic Nitinol.

13. The instrument according to claim 7 wherein the cutting ring halves permits conducting a swivel movement of almost 90° around an axis running crosswise to the fish joint.

14. An instrument for the surgical removal of a defective heart valve, comprising:
two body members arranged coaxially and at a distance to one another at or on an elongated member, a cutting element on each of the body members, the body members being able to move axially relative to one another in such a way that the respective cutting elements are aligned opposite one another to cut out a defective heart valve positioned between the body members;
the cutting elements of the body members having a radially collapsed position, in which their radial distance from the instrument axis becomes smaller, for the surgical introduction of the instrument into the surgical field;
two contact protective sheaths fitted to the elongated member, the contact sheaths having an engages position relative to the body members in which the cutting elements are collapsed and a disengaged position in which the contact sheath is pulled off axially from the body members, the contact sheaths movable axially to the engaged position and onto the respective body members to radially collapse the body members;
an advancing end of the instrument is movable through the defective heart valve until it is in a position in which one body member is found on one side of the defective heart valve and the other body member is found on the other side of the defective heart valve;
the contact protective sheaths in their disengaged position being pulled off axially from the body members so that the cutting elements of the body members have a radially expanded position;
wherein the cutting elements of each of the body members are formed of two semicircular cutting ring halves each having a center, the ring halves being joined to one another at respective ends thereof to form a circular cutting ring by means of opposed single-axis hinge joints that are comprised of diametrically disposed hinge members having aligned respective hinge axes that together define a common swivel axis, wherein each half of the cutting ring is made of an elastically deformable flat material strip and each is pre-shaped true to size in edge-wise format to the semicircle diameter required in the radially expanded state;
wherein the hinge axes of both of the hinge members of the circular cutting rings are aligned perpendicular to the axis of the elongated member;
each said body member also including two pairs of elastically deformable fish joints that are each resistant to extension and compression and that are each constructed of a flat material strip, the fish joints extending in the longitudinal direction of the elongated member and each being mounted at the elongated member at a foot end thereof;
said pairs of elastically deformable fish joints including;
a first pair of the elastically deformable fish joints being mounted on the elongated member at the foot end thereof, the head end of which is connected to the respective hinge joints of the hinge members of the semicircular-shaped cutting ring halves, the foot end of which are mounted to an axially sliding member;
a second pair of the elastically deformable fish joints being mounted on the elongated member at the foot end thereof, the head end of which is connected to the center of the semicircle on the semicircular-shaped cutting ring halves, the foot end of which are mounted in a stationary manner to the elongated member;
wherein the elastically deformable fish joints are constructed and arranged for a relative swivel movement of the cutting ring halves of almost 90° around the common swivel axis folding between the radially collapsed position and the radially expanded position.

15. The instrument according to claim 14 wherein the elastically deformable fish joints are constructed and arranged for a relative swivel movement of the cutting ring halves of almost 90° around an axis running crosswise to the fish joints.

16. The instrument according to claim 14, including a pair of sliding blocks for holding the foot end of respective first pair of elastically deformable fish joints, and a pair of bearing blocks for holding the foot end of respective second pair of elastically deformable fish joints.

17. The instrument according to claim 14, wherein the contact protective sheaths are moved axially onto the fish joints toward each other in order to collapse the body members, and are moved in the opposite direction away from each other in order to expand the body members.

18. The instrument according to claim 14, wherein a diameter of the cutting ring of one body member is slightly larger than a diameter of the cutting ring of the other body member, such that both cutting rings engage in one another with the formation of a narrow shearing gap when cutting out the defective heart valve positioned between them.

19. The instrument according to claim 14, wherein the body members with their cutting rings can rotate relative to one another in such a way that the defective heart valve is cut out by a rotating-punching process.

20. The instrument according to claim 14 wherein the elastically deformable flat material strip is of superelastic Nitinol.

* * * * *